United States Patent [19]
Struble et al.

[11] Patent Number: 5,242,407
[45] Date of Patent: Sep. 7, 1993

[54] INFUSION PUMP WITH IMPROVED CONTAMINATION RESISTANCE

[75] Inventors: Kent R. Struble, Mahtomedi; Rodney J. Smith, Hastings, both of Minn.

[73] Assignee: Minnesota Mining and Manufacturing Company, St. Paul, Minn.

[21] Appl. No.: 917,593

[22] Filed: Jul. 23, 1992

[51] Int. Cl.⁵ ............................................. A61M 1/00
[52] U.S. Cl. ................................... 604/151; 604/153; 604/131; 417/474
[58] Field of Search ............... 604/131, 132, 151, 152, 604/153, 154, 155; 417/474, 475, 476, 477; D24/232

[56] References Cited

U.S. PATENT DOCUMENTS

| | | | |
|---|---|---|---|
| D. 278,181 | 3/1985 | Archibald et al. | D24/8 |
| 4,191,184 | 3/1980 | Carlisle | 604/153 |
| 4,236,880 | 12/1980 | Archibald | 417/478 |
| 4,277,226 | 7/1981 | Archibald | 417/38 |
| 4,322,201 | 3/1982 | Archibald | 417/279 |
| 4,673,389 | 6/1987 | Archibald et al. | 604/81 |
| 4,913,703 | 4/1990 | Pasqualucci | 604/151 |
| 5,017,192 | 5/1991 | Dodge et al. | 604/250 |
| 5,032,112 | 7/1991 | Fairchild et al. | 604/151 |
| 5,078,362 | 1/1992 | Lawless et al. | 251/9 |
| 5,116,203 | 5/1992 | Natwick et al. | 417/53 |

OTHER PUBLICATIONS

Pages 10 and 11 of an Operator's Manual for the FLO--GARD 6200 Volumetric Infusion Pump from Travenol.
Brochure: Valleylab Infutrol. Now, You Don't Have to Work Under Pressure from Valleylab; Brochure No. 945-605-052 Jan. 1983.
Brochure: AVI 480 and 480CM Infusion Pump from Minnesota Mining and Manufacturing Company; Brochure No. 70-2008-4364-0 (1991).
Brochure: AVI 200A Infusion Pump from Minnesota Mining and Manufacturing Company; Brochure No. 70-2008-3439-1 (1988).
Brochure: AVI Micro 210A Infusion Pump from Minnesota Mining and Manufacturing Company; Brochure No. 70-2008-3437-5 (1988).
Brochure: AVI 400A Infusion Pump from Minnesota Mining and Manufacturing Company; Brochure No. 70-2008-3438-3 (1988).
Brochure: AVI 840 Dual Channel Infusion Pump from Minnesota Mining and Manufacturing Company; Brochure No. 70-2008-4780-7 (Sep. 1990).
Brochure: AVI 845 Dual Channel Infusion Pump from Minnesota Mining and Manufacturing Company; Brochure No. 70-2008-4874-8 (Nov. 1990).
Brochure: AVI 285 and 285CM Micro Infusion Pump from Minnesota Mining and Manufacturing Company; Brochure No. 70-2008-4363-2 (1991).
Brochure: AVI Nurse Clinician Services from Minnesota Mining and Manufacturing Company; Brochure No. 70-2008-4951-4 (1991).
Brochure: 3M IV Poles; 3M Delivers space-saving solutions from Minnesota Mining and Manufacturing Company; Brochure No. 70-2008-3930-9 (Dec. 1989).

(List continued on next page.)

Primary Examiner—John G. Weiss
Attorney, Agent, or Firm—Gary L. Griswold; Walter N. Kirn; Stephen W. Bauer

[57] ABSTRACT

An infusion pump for regulating the administration of intravenous fluids to a patient. The infusion pump includes a pump housing for holding the pumping mechanism, and a door for holding the IV tubing set in operably position relative to the pumping mechanism. The upper surface of the pump housing has a notch formed therein, and the upper surface of the door is positioned under the notch when the door is closed. The notch is sized and shaped so as to closely grip the IV tubing assembly around a portion of its circumference, so that liquid dripping down along the exterior of the IV tubing set from above the notch tends to be shunted away from the IV tubing. Liquid dripping through the notch tends is diverted onto the upper surface of the door and away from the pumping mechanism.

24 Claims, 3 Drawing Sheets

OTHER PUBLICATIONS

Brochure entitled "Plum—Introducing The Plum–LifeCare 5000 Drug Delivery System"; Abbott Laboratories; Brochure No. 86–200–20 Oct., 1988.

Brochure: LifeCare—Electronic Flow Control—System Operating Manual for LifeCare 5000 Plum Infusion System; Brochure No. 430–03388–009 (Jan. 1989).

Brochure: LIFECARE 5000Drug Delivery System.

Brochure: Geminin PC2 "Volumetric Pump/Controller from IMED"; 1987; Brochure No. IM7265/15M.

Brochure: Gemini PC1 "Volumetric Pump/Controller from IMED"; 1988; Brochre No. IM7531/10M.

Brochure: "FLO-GARD 6100 Volumetric Infusion Pump from Travenol Laboratories, Inc."; Brochure No. 431700 Jul. 1983.

INFUSION PUMP WITH IMPROVED CONTAMINATION RESISTANCE

This invention relates generally to infusion pumps used to regulate flow of fluid to a patient, and more particularly to such an infusion pump having improved resistance from liquid contamination of the pumping mechanism.

BACKGROUND OF THE INVENTION

In a modern hospital setting, it is common for patients to be treated with some form of infusion therapy. Typically, the fluid to be infused into the patient is supplied in a bottle or a flexible bag, which is connected to the patient by an IV tubing set. The IV tubing set typically depends on the pressure head supplied by gravity to infuse the patient with the fluid, and/or is adapted to interface with an infusion pump. Infusion pumps are often required, particularly if the infusate contains a dissolved medication that must be administered to the patient according to a particular regimen.

IV tubing sets conventionally use a vented spike to puncture the supply bag and allow the outflow of fluid through the IV tubing. The connection between spike and bag occasionally leaks fluid, which then tends to drip along the IV tubing. If an infusion pump is being used, the exterior of the tubing set may become a conduit by which the pumping mechanism can be contaminated by the leaking liquid. These liquids frequently include sticky sugars or powerful drugs, neither of which are desirable to have contaminating the moving parts of the pumping mechanism.

Various approaches for coping with this problem have been seen in commercial infusion pumps. For example, the "Travenol Flo-gard 6200" brand infusion pump, sold by Baxter International Inc., Deerfield, Ill., is loaded with the IV tubing making an inverted U-shaped curve so that there is a tubing segment which turns upward as it enters the pump enclosure. Leaking liquid drips off the tubing where the upward-turned segment begins, which is outside the pump enclosure. This arrangement is considered by some to be difficult to load.

In the "Gemini PC-1" and "Gemini PC-2" brand infusion pumps, sold by IMED Corporation, San Diego, Calif., the peristaltic pumping mechanism is covered by a flexible polymeric sheet to prevent contamination by dripping liquid. The "Gemini" brand pumps also include a groove formed in the handle for receiving the IV tubing and setting a bend in that tubing before it enters the pumping mechanism.

In the "Travenol Flo-gard 6100" brand infusion pump, sold by Baxter International Inc., Deerfield, Ill., an upper surface has a notch which helps orient the tubing assembly for proper loading into the pumping assembly.

In the "Valleylab Infutrol 6000" and "Valleylab Infutrol 6006" brand infusion pumps, sold by Ivion Corporation, Englewood, Colo., the tubing set includes a pumping cassette that is mounted on the infusion pump with both upstream and downstream sections of IV tubing extending downwardly from the cassette.

SUMMARY OF THE INVENTION

The invention provides an infusion pump for regulating fluid flow through the flow path of an IV tubing set; in which the infusion pump has improved resistance against contamination of its pumping/regulating mechanism by liquid; in which the improved contamination resistance is obtained without inconvenience to the operator; and in which the improved contamination resistance is automatically obtained when the door of the infusion pump is closed. The invention provides an infusion pump in which the pumping mechanism is kept clean while maintaining a simple, easy-to-load arrangement between the pumping mechanism and the IV tubing set.

Generally, the infusion pump of the invention comprises pumping means for pumping fluid through IV tubing placed in the infusion pump to regulate flow through the IV tubing, a pump housing holding the pumping means, and a door holding the IV tubing in operable engagement with the pumping means. The pump housing includes an upper surface having a tubing-receiving notch therein for receiving a portion of the IV tubing upstream from the pumping means. The tubing-receiving notch is sized and adapted to closely grip the IV tubing around a substantial portion of its circumference. A liquid-shedding surface is provided on the upper surface of the door, with the liquid-shedding surface being disposed at a higher elevation than the pumping mechanism. When the door is closed, the liquid-shedding surface is disposed under the upper surface and the tubing-receiving notch, and is adapted to engage the IV tubing mounted in the infusion pump along the side of the IV tubing opposite the closed end of the notch. The arrangement is such that liquid dripping down along the exterior of the IV tubing from above the tubing-receiving notch tends to be shunted away from the IV tubing along the upper surface of the pump housing and the liquid-shedding surface of the door, thereby diverting such liquid away from the pumping means.

Preferably, the closed end of the tubing-receiving notch is provided with a liquid-diverting ledge that engages the exterior of the IV tubing and diverts liquid toward the open end of the notch. The liquid-diverting ledge is preferably sloped in the direction toward the open end of the notch, and extends from the closed end of the notch beyond the back surface of the door.

Other features will be pointed out hereinafter.

BRIEF DESCRIPTION OF THE DRAWING

The invention will be further described with reference to the drawing wherein corresponding reference characters indicate corresponding parts throughout the several views of the drawing, and wherein.

DETAILED DESCRIPTION OF A PREFERRED EMBODIMENT

Figure 1:
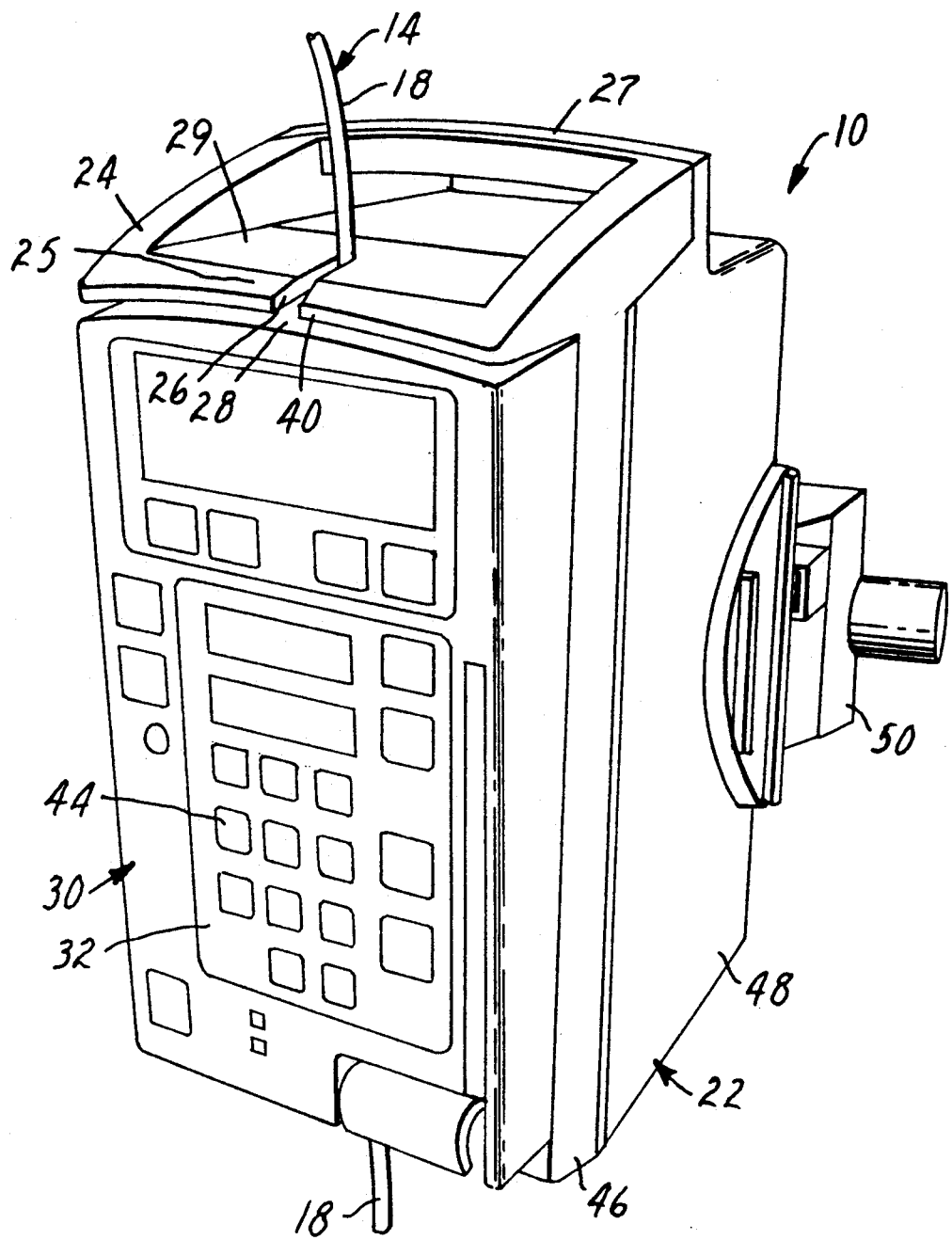
FIG. 1 is a perspective view of an infusion pump of the invention.
Figure 2:
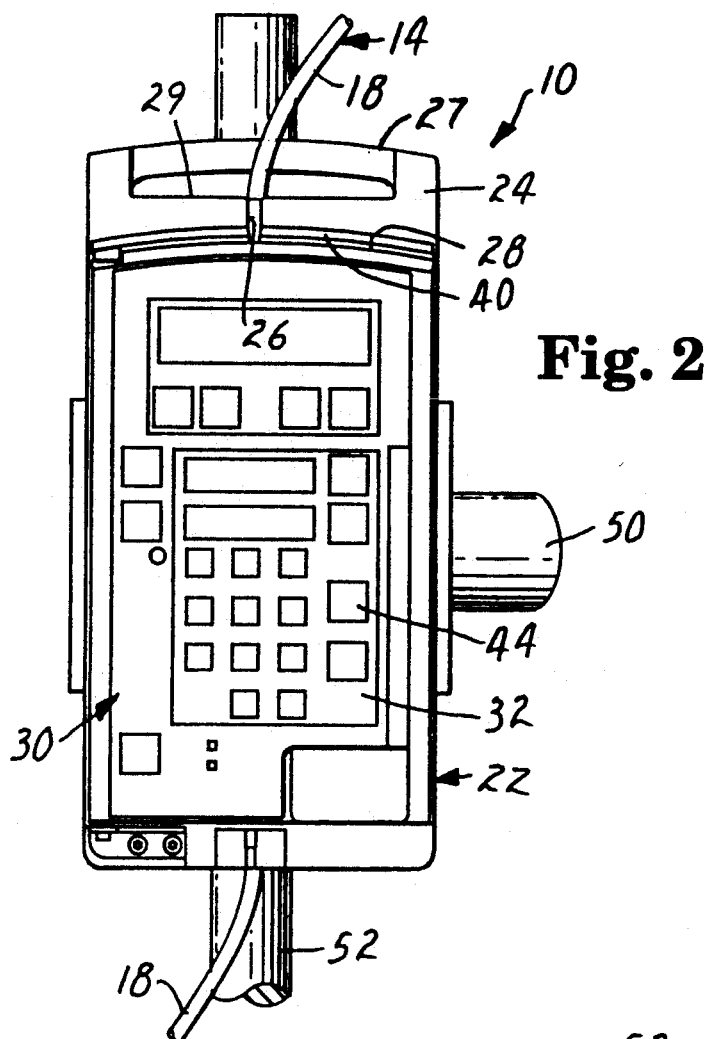
FIG. 2 is a front view of the infusion pump of FIG. 1.
Figure 3:
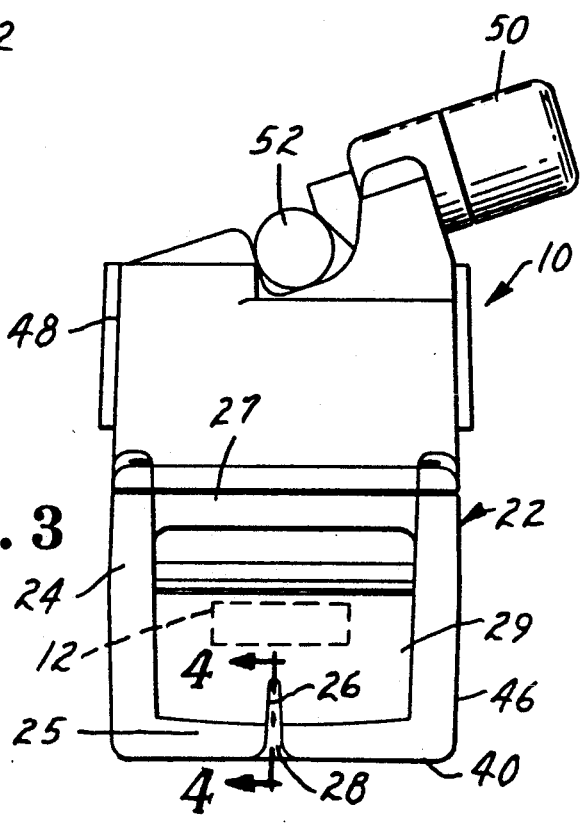
FIG. 3 is a top plan view of the infusion pump of FIGS. 1 and 2.

Now referring to the drawing, an infusion pump of the invention is designated in its entirety by the reference numeral 10. Infusion pump 10 includes a pumping mechanism 12 which may be of the general type described in co-assigned U.S. Pat. Nos. 4,236,880; 4,277,226 and 4,322,201, all of which are incorporated herein by reference. Infusion pumps 10 of this general type have been sold by Minnesota Mining and Manufacturing Company, St. Paul, Minn., under various trade designations including the "AVI 200" and "AVI 400" model series of infusion pumps.

Infusion pumps 10 of this type are adapted for use with IV tubing sets 14 of the type having a pumping cassette 16 (illustrated in cross-section in FIG. 4) mounted in line with IV tubing 18. While the cassette type of infusion pump is preferred, the infusion pump 10 may alternately be of the type commonly referred to as a "linear peristaltic pump", that is, infusion pumps that selectively squeeze straight portions of IV tubing to regulate or pump fluid through the IV tubing. In any event, the infusion pump 10 regulates fluid flow through the lumen of IV tubing 18 for controlled administration to a patient.

The infusion pump 10 generally comprises the pumping means 12 for pumping fluid through IV tubing 18 placed in the infusion pump 10 to regulate flow through the IV tubing 18, and a pump housing 22 for holding and at least partly enclosing the pumping means 12. The pumping means 12 preferably comprises a conventional pumping mechanism 12 for use with the cassette 16. The upper surface 24 of the pump housing 22 has a tubing-receiving notch 26 therein for receiving a portion of the IV tubing 18 upstream from the pumping mechanism 12. The tubing-receiving notch 26 is sized and adapted to closely grip the IV tubing 18 around a substantial portion of its circumference. A liquid-shedding surface 28 on the door 30 of the infusion pump 10 is disposed under the upper surface 24 and under the tubing-receiving notch 26 when the door 30 is closed.

The arrangement is such that the liquid-shedding surface 28 engages the side of the IV tubing 18 opposite the closed end 36 of the notch 26 such that liquid dripping down along the exterior of the IV tubing 18 from above the tubing-receiving notch 26 tends to be shunted away from the IV tubing 18 along the upper surface 24 and/or the liquid-shedding surface 28, thereby diverting such liquid away from the pumping mechanism 12.

The door 30 is pivotably mounted on the infusion pump 10 for movement between open and closed positions. In the open position, the cassette 16 may be loaded into or unloaded from the infusion pump 10. In the closed position, the door 30 is adapted to hold the pumping cassette 16 in operable engagement with the pumping mechanism 12. The upper surface (also 28) of the door 30 is positioned at a higher elevation that the pumping mechanism 12 in normal operation of the infusion pump 10. The liquid-shedding surface 28 is formed by at least a portion of the upper surface 28 of the door 30 and is positioned directly under the tubing-receiving notch 26 when the door 30 is closed, such that liquid dripping past the notch 26 tends to be diverted along the liquid-shedding surface 28 of the door 30.

The liquid-shedding surface 28 is sloped downwardly in the outward direction relative to the pump housing 22. More specifically, the liquid-shedding surface 28 is sloped in the forward direction toward the front of the infusion pump 10 so that external liquid tends to be diverted to the frontal external surface 32 of the infusion pump 10. The arrangement is preferably such that substantially the entire upper surface 28 of the door 30 is sloped downwardly in the outward/forward direction relative to the pump housing 22. Most preferably, the upper surface 28 of the door 30 is sloped downwardly at an angle of approximately 10–20 degrees (e.g., 10 degrees) relative to horizontal.

A tubing-receiving groove 33 is preferably formed in the pump housing 22, with the tubing-receiving groove 33 extending downwardly from the closed end 36 of the tubing-receiving notch 26 toward the pumping mechanism 12. The groove 33 is sized and configured to closely receive the IV tubing 18 such that the IV tubing 18 is substantially completely encircled by the groove 33 in combination with the portion of the back surface 38 of the door 30 that engages the tubing 18. It is contemplated as an alternative that the groove 33 could be sloped slightly rearwardly as it extends downwardly from the notch 26. As yet another alternative, it is contemplated that a similar groove (not shown) to groove 33 could be formed in the back surface 38 of the door 30.

Preferably, at least a substantial portion 25 of the upper surface 24 of the pump housing 22 generally adjacent the tubing-receiving notch 26 is sloped downwardly away from the tubing-receiving notch 26 to divert liquid away from the notch 26. The sloping portion 25 of the upper surface 24 of the pump housing 22 is sloped downwardly in the same outward/forward direction as the upper surface 28 of the door 30 is sloped so that liquid tends to be diverted along the frontal surface 32 of the infusion pump 10, which can be wiped clean from time to time.

Most preferably, the sloping portion 25 of the upper surface 24 of the pump housing 22 is sloped downwardly at an angle of approximately 1–40 degrees relative to horizontal. For example, the upper surface 24 of the infusion pump 10 may be formed along an arc having a radius of approximately 6.5 inches (165 mm). More specifically, the upper surface 24 may have a generally rounded configuration, sloping downwardly in the forward, outward direction so that the forward portion of this rounded surface 25 (adjacent front edge 40) is sloping downwardly at an angle of approximately 30 degrees, but the surface 25 is generally tangent to the horizontal along the upper surface of a handle 27. The upper surface 24 may also include hollowed out portion 29 that is sloped downwardly in the forward direction at a relatively shallow angle (e.g., approximately 2–4 degrees).

Figure 4:
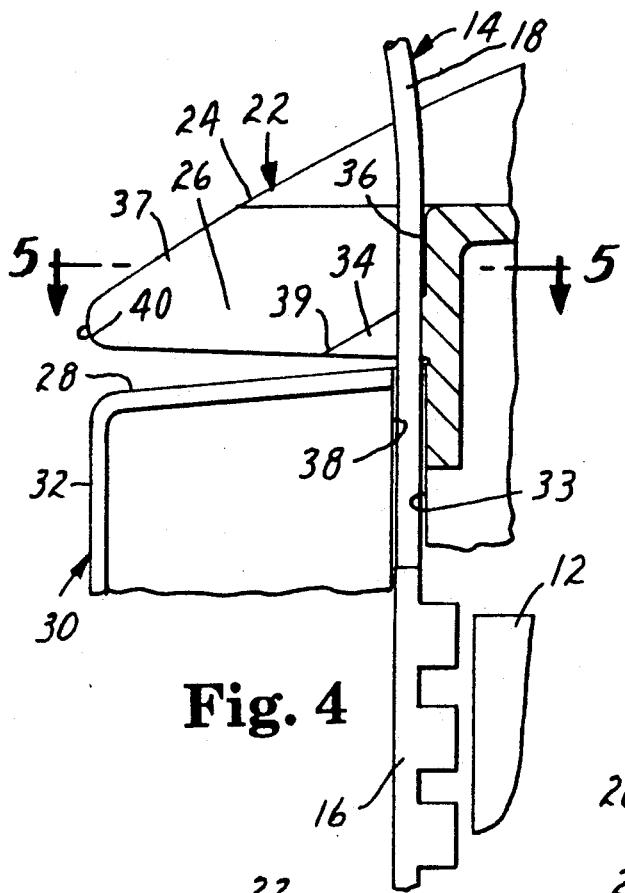
FIG. 4 is an enlarged cross-sectional view substantially along line 4—4 in FIG. 3.
Figure 5:
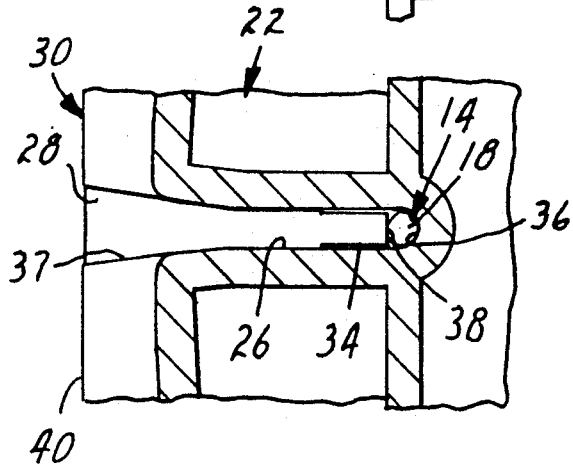
FIG. 5 is an enlarged cross-sectional view substantially along line 5—5 of FIG. 4, illustrating details of the notch.

As illustrated in FIGS. 4 and 5, the closed end 36 of the tubing-receiving notch 26 may be provided with a liquid-diverting ledge 34 which is adapted to engage the IV tubing 18 to divert liquid in the direction toward the open end 37 of the notch 26. The liquid-diverting ledge 34 preferably extends a small distance from the walls of the notch 26, and slopes downwardly in the direction toward the open end 37 of the notch 26 at an angle of approximately 60 degrees. It is contemplated that the liquid-diverting ledge 34 could be the only part of the notch 26 firmly engaging the IV tubing 18.

The ends 39 of the liquid-diverting ledge 34 preferably are disposed above the liquid-shedding surface 28 of the door 30 at a position forward of the back surface 38 of the door 30 when the door 30 is in its closed position. The arrangement is such that liquid dripping along the exterior of the IV tubing 18 is diverted forwardly along the ledge 34 so that it falls on the liquid-shedding surface 28 of the door 30.

The walls defining the notch 26 preferably converge in the direction toward the closed end 36 of the slot 26.

For example, the opposing notch-defining walls (also 26) may converge toward one another at an included angle of approximately 6 degrees.

The front edge 40 of the upper surface 24 of the pump housing 22 preferably extends forwardly over the top of the door 30, most preferably as far forward as the front surface 32 of the door 30. The front surface 32 of the door 30 may conveniently be provided with a sealed control panel 44 for user interface with the infusion pump 10.

The pump housing 22 may also be provided with a second tubing-receiving groove (not shown) similar to groove 33 to help place the cassette 16 in proper alignment with the pumping mechanism. The second groove and the first groove 33 may be generally C-shaped with the ends of the "C" projecting sufficiently to help retain the IV tubing 18 in position. A free flow prevention system (not shown), such as described in co-assigned U.S. Pat. No. 5,017,192 (incorporated herein by reference), may also be provided between the pumping mechanism 12 and the bottom of the pump housing 22.

Most preferably, the pump housing 22 is injection molded of thermoplastic material, such as acrylonitrile-butadiene-styrene (ABS), in two major half portions (a front portion 46 and a back portion 48) that are mechanically fastened together. The front portion 46 includes the sloping portions of the upper surface 24, the notch 26 and the ledge 34. The door 30 may conveniently be injection molded of the same thermoplastic material.

The infusion pump 10 preferably includes a clamping mechanism 50 for mounting the infusion pump 10 on a pole stand 52. A preferred mechanism 50 is described in co-assigned U.S. patent application Ser. No. 07/797,691, filed Nov. 25, 1991, which is incorporated herein by reference.

Figure 6:
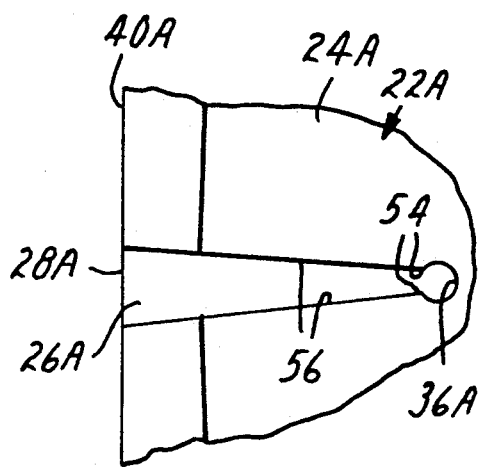
FIG. 6 is a view similar to FIG. 5 showing an alternative embodiment of the tubing-receiving notch.

FIG. 6 illustrates an alternative embodiment of the tubing-receiving notch, here designated 26A, in which the notch 26A has a generally keyhole outline when viewed from above. The notch 26A includes opposing projections 54 extending from the pump housing 22A into the notch 26A. These projections 54 and the closed end 36A of the notch 26A substantially define a round area (also 36A) substantially corresponding to the cross section of the IV tubing 18. These projections 54 are designed to provide a snap fit of the IV tubing 18 in the round area 36A. The projections 54 and the closed end 36A are configured to closely receive the IV tubing 18 so that most of the liquid dripping along the exterior of the IV tubing 18 is diverted from the IV tubing 18 by the upper surface 24A of the pump housing 22A. The side walls 56 of the pump housing 22A defining an inlet portion (also 56) of the notch 26A converge in the direction toward the closed end 36A of the notch 26A to facilitate moving the IV tubing 18 into the notch 26A.

OPERATION

In order to insert the cassette 16 of the IV tubing set 14 into the infusion pump 10, the door 30 is opened and the cassette 16 is placed on alignment pins (not shown) on the pumping mechanism 12 in proper alignment with the pumping mechanism 12, and the upstream portion of the IV tubing 18 is inserted into the tubing-receiving notch 26 and groove 33. The alignment pins may include slightly enlarged heads to help retain the cassette 16 in position. The door 30 is closed to secure the pumping cassette 16 in operable engagement with the pumping mechanism 12. As the door 30 is closed, the liquid-shedding upper surface 28 of the door 30 is moved directly under the notch 26 and the back surface 38 of the door 30 engages the IV tubing 18 under the notch 26.

In the event that liquid drips down along the exterior of the IV tubing 18 from above the notch 26, for example, from a leaking connection between an IV bag (not shown) and a spike connector (not shown), the upper surface 24 of the pump housing 22, the liquid-diverting ledge 34 and the upper surface 28 of the door 30 tend to divert the liquid away from the pumping mechanism 12. Because these surfaces 24 and 28 are sloped downwardly in the outward/forward direction, such external liquid tends to be passively diverted away from the pumping mechanism 12 under the force of gravity. The arrangement is such that the liquid tends to be diverted in the same direction along one major (front) surface of the infusion pump 10 so that such liquid can be cleaned up by wiping the front surface of the infusion pump 10.

More specifically, liquid dripping downwardly along the exterior of the IV tubing 18 is first diverted along the upper surface 24 of the pump housing 22 adjacent the notch 26 in a direction generally outwardly relative to the pumping mechanism 12 of the infusion pump 10. Since a substantial portion of the circumference of the IV tubing 18 is closely gripped in the notch 26, most of the liquid dripping down along the IV tubing 18 tends to be diverted by the upper surface 24 of the pump housing 22 and the liquid-diverting ledge 34. To the extent the liquid is allowed to keep dripping along the exterior of the IV tubing 18, it is channeled by the notch 26 and/or the liquid-diverting ledge 34 along the front portion of the IV tubing 18, where the liquid is more likely to be diverted by the upper surface 28 of the door 30 in the direction away from the IV tubing 18 and the pumping mechanism 12.

As various changes could be made in the above constructions and methods without departing from the scope of the invention, it is intended that all matter contained in the above description or shown in the accompanying drawing be interpreted as illustrative and not in a limiting sense.

What is claimed is:

1. An infusion pump for regulating fluid flow through the flow path of an IV tubing set having IV tubing, the infusion pump comprising:

pumping means for pumping fluid through IV tubing placed in the infusion pump to regulate flow through the IV tubing;

a pump housing holding the pumping means, the pump housing including an upper surface having a tubing-receiving notch therein for receiving a portion of the IV tubing upstream from the pumping means, the notch having an open end through which IV tubing may be inserted and a closed end sized and adapted to closely grip the IV tubing around a substantial portion of its circumference; and a door mounted on the pump housing for holding the IV tubing set in operable engagement with the pumping means, the door including a liquid-shedding surface positioned at a higher elevation than the pumping means and disposed under the upper surface of the pump housing and under the tubing-receiving notch when the door is closed, such that the liquid-shedding surface is adapted to engage the IV tubing along the side of the IV tubing opposite the closed end of the notch at an elevation below the upper surface of the pump housing and above the pumping means, so that liquid dripping down along the exterior of the IV tubing from above the tubing-receiving notch tends to be shunted away from the IV tubing along the upper surface or the liquid-shedding surface, thereby diverting such liquid away from the pumping means.

2. An infusion pump according to claim 1 adapted to receive an IV tubing set of the type including a pumping cassette, the door being adapted to hold the pumping cassette in operable engagement with the pumping means, the door having an upper surface positioned at a higher elevation that the pumping means in normal operation of the infusion pump, the liquid-shedding surface being at least a portion of the upper surface of the door and being positioned directly under the notch when the door is closed such that liquid dripping past the notch tends to be diverted along the liquid-shedding upper surface of the door.

3. An infusion pump according to claim 2 wherein the liquid-shedding surface is sloped downwardly in the outward direction relative to the pump housing.

4. An infusion pump according to claim 3 wherein substantially the entire upper surface of the door is sloped downwardly in the outward direction relative to the pump housing, and at least a substantial portion of the upper surface of the pump housing generally adjacent the tubing-receiving notch is sloped downwardly away from the tubing-receiving notch.

5. An infusion pump according to claim 3 wherein the closed end of the tubing-receiving notch is provided with a liquid-diverting ledge adapted for closely engaging the IV tubing and diverting liquid in the direction away from the closed end.

6. An infusion pump according to claim 4 wherein the liquid-diverting ledge is sloped downwardly in the direction away from the closed end of the notch.

7. An infusion pump according to claim 6 wherein the sloping portion of the upper surface of the pump housing is sloped downwardly at an angle of approximately 10-40 degrees relative to horizontal, and the upper surface of the door is sloped downwardly at an angle of approximately 10-20 degrees relative to horizontal.

8. An infusion pump according to claim 1 wherein the door is pivotably mounted on the infusion pump and is adapted to hold the IV tubing set in operable engagement with the pumping means, the door having an upper surface positioned at a higher elevation than the pumping means in normal operation of the infusion pump, the liquid-shedding surface being at least a portion of the upper surface of the door.

9. An infusion pump according to claim 8 wherein the liquid-shedding surface is sloped downwardly in the outward direction relative to the pump housing.

10. An infusion pump according to claim 9 wherein substantially the entire upper surface of the door is sloped downwardly in the outward direction relative to the pump housing, and at least a substantial portion of the upper surface of the pump housing generally adjacent the tubing-receiving notch is sloped downwardly in the outward direction.

11. An infusion therapy system for regulating fluid flow to a patient, the system comprising an IV tubing set having IV tubing, and an infusion pump for regulating fluid flow through the IV tubing set, the infusion pump comprising:

pumping means for pumping fluid through the IV tubing to regulate flow through the IV tubing;

a pump housing holding the pumping means, the pump housing including an upper surface having a tubing-receiving notch therein for receiving a portion of the IV tubing upstream from the pumping means, the notch having an open end through which IV tubing may be inserted and a closed end sized and adapted to closely grip the IV tubing around a substantial portion of its circumference; and a door mounted on the pump housing for holding the IV tubing set in operable engagement with the pumping means, the door including a liquid-shedding surface disposed at a higher elevation than the pumping means and so disposed under the upper surface of the pump housing and the tubing-receiving notch when the door is closed that the liquid-shedding surface engages the IV tubing along the side facing the open end of the tubing-receiving notch, such that liquid dripping down along the exterior of the IV tubing from above the tubing-receiving notch tends to be shunted away from the IV tubing along the upper surface and/or the liquid-shedding surface, thereby diverting such liquid away from the pumping means.

12. A system according to claim 11 wherein the IV tubing set includes a pumping cassette having pumping chambers in fluid communication with the IV tubing, and the door of the infusion pump holding the pumping cassette in operable engagement with the pumping means when the door is closed, the door having an upper surface positioned at a higher elevation that the pumping means in normal operation of the infusion pump, the liquid-shedding surface being at least a portion of the upper surface of the door and being positioned directly under the notch such that liquid dripping through the notch tends to be diverted along the liquid-shedding surface of the door in the direction away from the IV tubing and pumping mechanism.

13. A system according to claim 12 wherein the liquid-shedding surface is sloped downwardly in the outward direction relative to the pump housing.

14. A system according to claim 13 wherein substantially the entire upper surface of the door is sloped downwardly in the outward direction relative to the pump housing.

15. A system according to claim 13 wherein at least a substantial portion of the upper surface of the pump housing generally adjacent the tubing-receiving notch is sloped downwardly in the outward direction.

16. A system according to claim 15 wherein the tubing-receiving notch further includes a liquid-diverting ledge in the notch for engagement with the IV tubing to divert liquid dripping along the IV tubing in the direction away from the closed end of the notch, the liquid-diverting ledge being sloped downwardly in the direction toward the open end of the notch.

17. A system according to claim 16 wherein the sloping portion of the upper surface of the pump housing is sloped downwardly at an angle of approximately 10-40 degrees relative to horizontal, and the upper surface of the door is sloped downwardly at an angle of approximately 10-20 degrees relative to horizontal.

18. A system according to claim 11 wherein the door is pivotably mounted on the infusion pump, the door having an upper surface positioned at a higher elevation than the pumping means in normal operation of the infusion pump, the liquid-shedding surface being at least a portion of the upper surface of the door.

19. A system according to claim 18 wherein the liquid-shedding surface is sloped downwardly in the outward direction relative to the pump housing.

20. A system according to claim 19 wherein substantially the entire upper surface of the door is sloped downwardly in the outward direction relative to the pump housing, and at least a substantial portion of the upper surface of the pump housing generally adjacent the tubing-receiving notch is sloped downwardly in the outward direction.

21. A method for preventing contamination of the pumping mechanism of an infusion pump of the type used to regulate fluid flow through an IV tubing set including IV tubing, the method comprising the following steps:
 providing an upper surface of the infusion pump with a notch therein for receiving a portion of the IV tubing upstream from the pumping mechanism, the notch being sized and adapted to closely grip the IV tubing around a substantial portion of its circumference;
 providing a liquid-shedding upper surface on a door of the type mounted on the infusion pump for holding the IV tubing set in operable engagement with the pumping mechanism of the infusion pump, the liquid-shedding upper surface of the door being disposed under the upper surface of the infusion pump and under the notch;
 dripping liquid down along the exterior of the IV tubing from above the notch;
 diverting liquid dripping downwardly along the exterior of the IV tubing along the upper surface of the infusion pump adjacent the notch in a direction generally outwardly relative to the pumping mechanism of the infusion pump; and
 diverting liquid along the liquid-shedding upper surface of the door such that the liquid tends to be shunted away from the IV tubing and the pumping mechanism.

22. A method according to claim 21 wherein the upper surface of the infusion pump and the liquid-shedding upper surface of the door are sloped downwardly in the direction generally outwardly from the pumping mechanism, the steps of diverting liquid along the upper surface of the infusion pump and diverting liquid along the liquid-shedding upper surface of the door each comprising diverting such liquid along the respective surfaces downwardly and outwardly away from the pumping mechanism under the force of gravity.

23. A method according to claim 22 wherein a substantial portion of the circumference of the IV tubing is closely gripped in the notch, the step of diverting liquid along the upper surface of the infusion pump including diverting liquid dripping along the aforesaid substantial portion of the IV tubing along the upper surface of the infusion pump.

24. A method according to claim 23 further comprising the step of closing the door such that the liquid-shedding upper surface of the door is positioned directly under the notch in engagement with the IV tubing so that liquid dripping through the notch tends to be diverted along the liquid-shedding upper surface of the door in the direction away from the IV tubing and pumping mechanism.

* * * * *